United States Patent [19]

Sawada et al.

[11] Patent Number: 5,091,418

[45] Date of Patent: Feb. 25, 1992

[54] ALPHA-GLUCOSIDASE INHIBITOR, PRADIMICIN Q

[75] Inventors: Yosuke Sawada, Tokyo; Tomokazu Ueki, Kanagawa; Takashi Tsuno, Tokyo; Toshikazu Oki, Yokohama, all of Japan

[73] Assignee: Bristol-Myers Squibb Company, New York, N.Y.

[21] Appl. No.: 589,729

[22] Filed: Sep. 28, 1990

[51] Int. Cl.$^5$ .............................................. A61K 31/19
[52] U.S. Cl. .................................... 514/569; 552/201; 552/220
[58] Field of Search ................. 552/220, 201; 514/569

[56]  References Cited
U.S. PATENT DOCUMENTS 3,721,684  3/1973  Meyers et al. ...................... 552/220

FOREIGN PATENT DOCUMENTS 2-83351  3/1990  Japan .................................. 552/201

Primary Examiner—Marianne Cintins
Assistant Examiner—Kimberly J. Kestler
Attorney, Agent, or Firm—Mollie M. Yang

[57]  ABSTRACT

The present invention relates to a novel α-glucosidase inhibitor, pradimicin Q, having the following formula

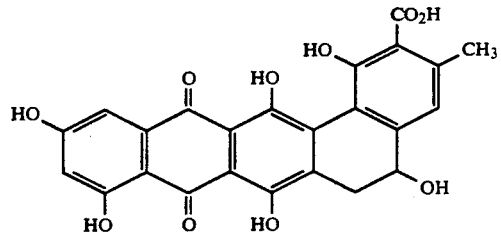

and its pharmaceutically acceptable base salts.

2 Claims, No Drawings

ALPHA-GLUCOSIDASE INHIBITOR, PRADIMICIN Q

BACKGROUND OF THE INVENTION

The present invention relates to a benzo[a]naphthacene compound having α-glucosidase inhibiting activity. The compound of the present invention is therefore useful as human and animal medicament for the treatment of conditions in which it is desirable to suppress α-glucosidase action, or to inhibit the increase of blood glucose level; such conditions include, for example diabetes, prediabetes, obesity, and adiposity.

Recently, Japanese Kokai 2-83351, published Mar. 23, 1990, reported the isolation of a novel α-glucosidase inhibitor from fermentation broth of Actinomycetes Strain MH193-16F4. The inhibitor, benanomicin C, has the following structure formula

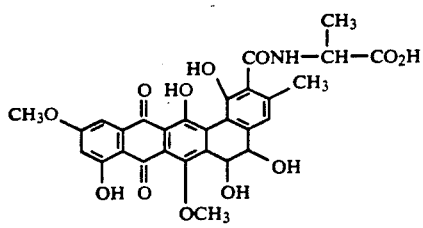

Although benanomicin C also possesses a benzo[a]naphthacene ring nucleus, its substituents differ substantially from those of the compound of the present invention. Furthermore, the compound of the present invention exhibits unexpectedly high α-glucosidase inhibitory activity compared to benanomicin C.

SUMMARY OF THE INVENTION

The present invention provides a novel α-glucosidase inhibitor designated pradimicin Q having the formula (I)

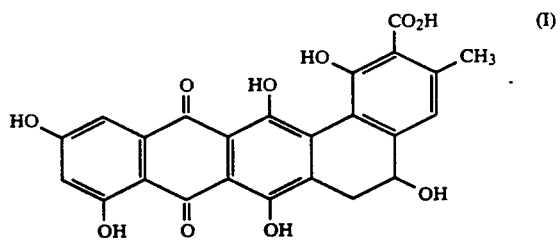

and its pharmaceutically acceptable base salts.

Another aspect of the present invention provides a process for producing pradimicin Q which comprises cultivating a strain of pradimicin Q producing Actinomadura verrucosospora subsp. neohibisca under submerged and aerobic conditions in a medium containing assimilable sources of carbon and nitrogen, and recovering from said medium pradimicin Q.

A further aspect of the present invention provides a pharmaceutical composition comprising pradimicin Q and a pharmaceutically acceptable vehicle.

Yet a further aspect of the present invention provides a method for inhibiting an increase in blood glucose level in an animal, including humans, which comprises administering to said animal in need of such treatment a therapeutically effective amount of pradimicin Q.

DETAILED DESCRIPTION OF THE INVENTION

One aspect of the present invention provides the compound pradimicin Q and its pharmaceutically acceptable base salts. "Pharmaceutically acceptable base salts" includes, but is not limited to, salts formed with inorganic bases such as sodium hydroxide, potassium hydroxide, sodium carbonate, calcium carbonate, magnesium hydroxide, and the like, or with organic bases such as diethylamine, ethylenediamine, triethylamine, ethanolamine, and the like.

Pradimicin Q is produced by cultivating pradimicin Q producing strain of Actinomadura verrucosospora subsp. neohibisca, or a variant thereof, or a mutant thereof, in a medium containing sources of assimilable carbon and nitrogen.

A strain capable of producing pradimicin Q is Actinomadura verrucosospora subsp. neohibisca strain R103-3. Another pradimicin Q producing strain is a mutant strain, herein designated as strain A10102, derived from strain R103-3. The characterizing properties of both strains are provided hereinbelow.

A. Producing Organism (i) Strain R103-3 was isolated from a soil sample collected in Puerto Viejo Costa, Peru. A biologically pure culture of strain R103-3 was deposited with the American Type Culture Collection, Rockville, Md. under accession number ATCC 53930. This culture has been accepted for deposit under the BUDAPEST TREATY ON THE INTERNATIONAL RECOGNITION OF THE DEPOSIT OF MICROORGANISMS FOR THE PURPOSES OF PATENT PROCEDURE.

The morphological, cultural, physiological, and chemotaxonomical characteristics of strain R103-3 are similar to those of Actinomadura verrucosospora, but strain R103-3 is differentiated from Actinomadura verrucosospora in the formation of red diffusible pigments and other physiological characteristics Therefore, strain R103-3 was designated Actinomadura verrucosospora subsp. neohibisca subsp. nov.

(a) Morphology

Strain R103-3 forms short or rudimental aerial mycelium and well-branched non-fragmentary substrate mycelium. Loop or spiral short spore-chains (5–12 spores per chain) are formed on the aerial hyphae. The spores are oval (0.8×1.2–1.5 μm), non-motile, and have a warty surface.

(b) Cultural and Physiological Characteristics

The cultural and physiological characteristics were examined by the methods of Shirling and Gottlieb (Int. J. Syst. Bacteriol., 1966, 16:313–340), and Gordon, et al. (J. Gen. Microbiol., 1978, 109:69–78).

Strain R103-3 forms aerial mycelium and spore-chain in ISP media Nos. 3, 4, 5, and 7 and produces abundantly reddish diffusible pigments (pradimicins) in Czapek's agar and natural organic media, such as ISP medium No. 2. Cultural and physiological characteristics are shown in Tables 1 and 2, respectively.

TABLE 1

| Cultural Characteristics of Strain R103-3 | | | | |
|---|---|---|---|---|
| Medium | Growth | Aerial Mycelium | Substrate Mycelium | Diffusible Pigment |
| Sucrose-nitrate agar (Czapek-Dox agar) | Moderate | None | Very deep red (14) | Very deep purplish red (257) |
| Tryptone-yeast | Poor, not | None | Deep red | Moderate |

TABLE 1-continued
Cultural Characteristics of Strain R103-3

| Medium | Growth | Aerial Mycelium | Substrate Mycelium | Diffusible Pigment |
|---|---|---|---|---|
| extract broth (ISP No. 1) | turbid | | (13) | red (15) |
| Yeast extract-malt extract agar (ISP No. 2) | Good | None | Very deep red (14) | Very dark red (17) |
| Oatmeal agar (ISP No. 3) | Moderate | Moderate; pale pink (7) | Moderate pink (5) | Grayish pink (8) to light grayish red (18) |
| Inorganic salts-starch agar (ISP No. 4) | Moderate | Poor; white | Moderate pink (5) | Light grayish red (18) |
| Glycerol-asparagine agar (ISP No. 5) | Poor | Poor; white | Colorless | None |
| Peptone-yeast extract-iron agar (ISP No. 6) | Good | Scant; white | Grayish pink (8) to deep red (13) | Very deep red (14) |
| Tyrosine agar (ISP No. 7) | Moderate | Poor; white | Moderate red (15) | Light yellowish pink (28) |
| Glucose-asparagine agar | Poor | None | Colorless | Light pink (4) |
| Nutrient agar | Moderate | Poor; white | Dark pink (6) | Dark red (16) |
| Bennett's agar | Good | None | Blackish red (21) | Blackish red (21) |

Observation after incubation at 28° for 3 weeks.
Color Name: ISCC-NBS color-name charts.

TABLE 2
Physiological Characteristics of Strain R103-3

| Decomposition of: | | Acid Production from*: | |
|---|---|---|---|
| Adenine | − | Adonitol | − |
| Casein | + | D-Arabinose | − |
| Hippuric acid | + | L-Arabinose | + |
| Hypoxanthine | + | Cellobiose | + |
| Tyrosine | + | Dulcitol | − |
| Xanthine | − | Erythritol | − |
| Decarboxylation of: | | D-Fructose | + |
| Benzoate | − | D-Galactose | − |
| Citrate | − | D-Glucose | + |
| Mucate | − | Glycerol | − |
| Succinate | + | Inositol | − |
| Tartrate | − | Lactose | − |
| Production of: | | D-Mannitol | + |
| Amylase | − | D-Mannose | − |
| Esculinase | + | D-Melezitose | − |
| Gelatinase | + | Melibiose | − |
| Nitrate reductase | + | Methyl-α-glucoside | − |
| Tyrosinase | − | Raffinose | − |
| Urease | − | L-Rhamnose | + |
| Growth in: | | D-Ribose | + |
| Lysozyme, 0.001% | − | Salicine | + |
| NaCl, 1%–7% | + | Soluble starch | + |
| 8% | − | D-Sorbitol | − |
| pH, 5.8–11.0 | + | L-Sorbose | − |
| 25°C.–39°C. | + | Sucrose | + |
| 22°C. and 42°C. | − | Trehalose | − |
| | | D-Xylose | + |

*Basal Medium: Pridham-Gottlieb medium (ISP No. 9), omitted CuSO$_4$.7H$_2$O

(c) Chemotaxonomy

The whole cell hydrolyzate of strain R103-3 contains meso-diaminopimelic acid, glucose, and madurose. Hence, the strain belongs to cell wall type III and sugar pattern B. The phopholipids contain phosphatidylglycerol and phosphatidylinositol without nitrogenous phospholipids and, hence, is placed in type P-I.

(d) Taxonomic Position

Based on the morphology and chemotaxonomy of strain R103-3, the strain is placed in the genus Actinomadura. Among hitherto described known species of Actinomadura. strain R103-3 is physiologically most similar to *Actinomadura verrucosospora*, but it is differentiated from the latter in its production of red diffusible pigment, resistance to NaCl, and negative acid formation from glycerol, lactose, and trehalose. Thus, strain R103-3 Was designated *Actinomadura verrucosospora* subsp. *neohibisca* subsp. nov.

Strain R103-3 is also distinct from *Actinomadura hibisca* known producer of pradimicins. Table 3 shows the differential characteristics of *Actinomadura hibisca* strain P157-2 (ATCC No. 53557) and strain R103-3 ATCC No. 53930.

TABLE 3
Differential Characteristics of *Actinomadura verrucosospora* Subsp. *neohibisca* Strain R103-3 from *Actinomadura hibisca* Strain P157-2

| | Strain R103-3 | Strain P157-2 |
|---|---|---|
| Morphology: | | |
| Spore-chain | Short, hook | Long, straight |
| Spore surface | Warty | Smooth |
| Cultural and physiological characteristics: | | |
| Tyrosine agar: | | |
| Brownish pigment | Not Formed | Formed |
| Glucose-asparagine agar: | | |
| Growth | Poor | Abundant |
| Reddish pigment | Scant | Abundant |
| Utilization of: | | |
| L-Arabinose | + | − |
| D-Mannitol | + | − |
| L-Rhamnose | + | − |
| D-Xylose | + | − |

(ii) Strain A10102 is derived from strain R103-3 by mutation using N'-methyl-N'-nitro-N-nitrosoguanidine (NTG). A biologically pure culture of A10102 was deposited with the American Type Culture Collection under accession number ATCC 55092. This culture has been accepted for deposit under the *BUDAPEST TREATY ON THE INTERNATIONAL RECOGNITION OF THE DEPOSIT OF MICROORGANISMS FOR THE PURPOSES OF PATENT PROCEDURE.* The procedure for mutation of strain R103-3 and for the screening of the mutant strains is described below.

Strain R103-3 was grown at 28° C. for 14 days on a modified Bennett's agar consisting of soluble starch 0.5%, glucose 0.5%, fish meat extract 0.1%, yeast extract 0.1%, NZ-case 0.2%, NaCl 0.2%, CaCO$_3$ 0.1%, and agar 1.6%; pH 7.0. Spores of the strain were suspended in saline, dispersed by sonication for 20 seconds in ice-bath, harvested by centrifugation at 3,500 rpm for 10 minutes at 25° C., and resuspended in 10 mM Tris-HCl, pH 9.0. The spore suspension (3 ml) was mixed with 3 ml of NTG solution (5,000 μg/ml in a mixture of water-dimethyl sulfoxide 9:1 (v/v)). The mixture was gently shaken at 28° C. for 1 hour. The NTG-treated spores were harvested by centrifugation, resuspended in saline, spread on a new agar plate, and incubated at 28° C. for 7 days. Each colony was picked up, inoculated to a fresh agar plate, and incubated at 28° C. for 7 days to be used as a mother culture plate. Each culture was transferred to 10 ml of the vegetative medium (Medium A) consisting of Na L-glutamate 0.1%, L-methionine 0.05%, L-arginine 0.05%, soluble starch 1.0%, glucose 1.0%, (NH$_4$)$_2$SO$_4$ 0.01%, K$_2$HPO$_4$ 0.6%, MgSO$_4$.7H$_2$O 0.05%, NaCl 0.05%, CaCO$_3$ 0.3%, salt solution (FeSO$_4$.7H$_2$O 0.1 g, ZnSO$_4$.7H$_2$O 0.1 g, MnCl$_2$.4H$_2$O 0.1 g, in 1 liter of water) 1% v/v, pH 7.0. The culture was incubated at 28° C. for 14 days on a shaker operating at 200 rpm. Pradimicin Q was identified by silica gel TLC (Merck) using a solvent system of methyl acetate/n-propanol/28% ammonium hydroxide (45:105:60), Rf for pradimicin Q was 0.2–0.25. As a result of the screening, a mutant strain designated as A10102 was found to produce pradimicin Q as its major fermentation product.

(a) Morphology

Both parent and its mutant strains form tufts of loop or spiral short spore-chains (5 to 10 spores per chain) on the short aerial mycelium. The spores are oval (0.8 × 1.3 μm), non-motile, and have a warty surface.

(b) Cultural Characteristics

Unlike parental strain R103-3, mutant strain A10102 produces reddish-purple pigments in ISP Media Nos. 2, 3, and 7 and brownish-black pigment in ISP Medium No. 6 (Table 4).

TABLE 4

Characterization of Cultural Differences Among R103-3 and A10102

| Cultural Characteristics | | Strain R103-3 | No. A10102 |
|---|---|---|---|
| Malt extract-yeast extract agar (ISP No. 2) | G | +++; Very dark red (17) | ++; Blackish red (21) |
| | A | None | None |
| | D | Very deep red (14) | Very dark purplish red (260) |
| Oatmeal agar (ISP No. 3) | G | ++; Pinkish white (9) | ++; Reddish purple (241) |
| | A | Scant; white | Scant; white |
| | D | Pinkish white (9) | Light reddish purple (240) |
| Inorganic salts-starch agar (ISP No. 4) | G | +; Pale yellowish pink (31) | +; Light reddish purple (240) |
| | A | Scant; white | Scant; white |
| | D | Pale yellowish pink (31) | Light reddish purple (240) |
| Peptone-yeast extract-iron agar (ISP No. 6) | G | ++; Grayish red (19) | +++; Brownish black (65) |
| | A | None | None |
| | D | None | Brownish black (65) |
| Tyrosine agar (ISP No. 7) | G | ++; Moderate yellowish pink (28) | ++; Pale reddish purple (244) |
| | A | Poor; white | Poor; white |
| | D | Pale yellowish pink (31) | Pale reddish purple (244) |
| Glucose-asparagine agar | G | ±; Colorless | ±; Colorless |
| | A | None | None |
| | D | None | None |

Observation after incubation at 28° C. for 2 weeks.
Color Name: ISCC-NBS color-name charts.
Abbreviations: G, growth (+++ good, ++ moderate, + poor, ± scant) and reverse color; A, aerial mycelium; and D, diffusible pigment.

(c) Physiological Characteristics

Mutant strain A10102 shows almost the same physiological reactions as the parental strain (Table 5).

TABLE 5

Physiological Characteristics of Strains R103-3 and A10102

| | Strain R103-3 | Strain A10102 |
|---|---|---|
| Hydrolysis of: | | |
| Gelatin | + | + |
| Soluble starch | − | − |
| Potato starch | − | − |
| Production of: | | |

TABLE 5-continued

Physiological Characteristics of Strains R103-3 and A10102

| | Strain R103-3 | Strain A10102 |
|---|---|---|
| Nitrate reductase* | −/+ | −/+ |
| Utilization of**: | | |
| Glycerol | + (w) | − |
| D-Arabinose | − | − |
| L-Arabinose | + | + |
| D-Xylose | + | + |
| D-Ribose | + | + |
| L-Rhamnose | + | + |
| D-Glucose | + | + |
| D-Galactose | + (w) | + (w) |
| D-Fructose | + | + |
| D-Mannose | − | − |
| L-Sorbose | − | − |
| Sucrose | − | − |
| Lactose | − | − |
| Cellobiose | + | + |
| Melibiose | − | − |
| Trehalose | + | + (w) |
| Raffinose | − | − |
| D-Melezitose | − | − |
| Soluble starch | + | + (w) |
| Cellulose | − | − |
| Dulcitol | − | − |
| Inositol | − | − |
| D-Mannitol | + | + |
| D-Sorbitol | − | − |
| Salicin | + | + |

*Czapek's sucrose-nitrate broth/Peptone-nitrate broth.
**Basal Medium: Pridham-Gottlieb medium.
+(w): Weakly Positive; −/+: Marginal Utilization B. Antibiotic Production Strains R103-3 and A10102 produce the novel compound pradimicin Q, along with other pradimicins A, B, C, D, E and L, when cultivated in a conventional medium. The producing organism is grown in a nutrient medium containing known nutritional sources for actinomycetes, i.e., assimilable sources of carbon and nitrogen added with optional inorganic salts and other known growth factors. Submerged aerobic conditions are preferably employed for the production of large quantities of antibiotic, although surface cultures and bottles may also be used for production of limited amounts. The general procedures used for the cultivation of other actinomycetes are applicable to the present invention.

The nutrient medium should contain an appropriate assimilable carbon source, such as ribose, glucose, sucrose, and cellobiose. As a nitrogen source, ammonium chloride, ammonium sulfate, urea, ammonium nitrate, sodium nitrate, etc., may be used either alone or in combination with organic nitrogen sources, such as peptone, meat extract, yeast extract, corn steep liquor, soybean meal, cotton seed meal, etc. There may also be added, if necessary, nutrient inorganic salts to provide sources of sodium, potassium, calcium, ammonium, phosphate, sulfate, chloride, bromide, carbonate, zinc, magnesium, manganese, cobalt, iron, and the like.

Production of the antibiotic complex comprising pradimicin components may be effected at any temperature suitable for satisfactory growth of the producing organism, e.g., 25°–40° C., and is most conveniently carried out at a temperature of around 27°–32° C. Ordinarily, optimum antibiotic production is obtained by flask fermentation after shaking with incubation periods of 5 to 12 days. If fermentation is to be carried out in tank fermentors, it is desirable to use a vegetative inoculum in a nutrient broth from a slant culture or a lyophilized culture. After obtaining an active inoculum in this manner, it is aseptically transferred to the fermentation medium in a tank fermentor Antibiotic production in tank fermentors usually reached a maximum after 3-6 days of incubation. Agitation in the tank fermentor is provided by stirring, and aeration may be achieved by injection of air or oxygen into the agitated mixture. Antibiotic production was monitored by HPLC followed with spectroscopic techniques, or by a conventional biological assay.

Pradimicin complex thus produced may be recovered from the fermentation broth, and pradimicin Q of the present invention separated, by any suitable methods for such recovery and separations; examples of these methods include extraction, precipitation, chromatography, and other art recognized conventional techniques. A preferred isolation and purification sequence for pradimicin Q is given in Examples 2 and 3.

It is to be understood that, for the production of pradimicin Q, the present invention is not limited to the particular organisms mentioned above but includes the use of variants and mutants thereof that retain the antibiotic-producing capability. Such variants and mutants can be produced from parent strains by various means, such as X-ray radiation, UV-radiation, and chemical mutagens, such as N-methyl-N'-nitro-N-nitrosoguanidine.

Thus, another aspect of the present invention provides a method for producing pradimicin Q which comprises cultivating an antibiotic-producing strain of *Actinomadura verrucosospora* subsp. *neohibisca* under submerged and aerobic conditions in a medium containing assimilable carbon and nitrogen sources. Preferably, the antibiotic-producing strains are strain R103-3, ATCC No. 53930, and strain A10102, ATCC No. 55092.

α-Glucosidase Inhibitory Activity

Forty μl of α-glucosidase (Sigma G-5003 #11 U/mg protein) (0.1 mg/ml in 100 mM phosphate buffer, pH 6.8=0.44 U/assay) for tests (or the buffer for the control), 950 μl of 0.7 mM p-nitrophenyl-α-D-glucopyranoside (Sigma N1377), and 10 μl of the assay compound (various concentrations dissolved in DMSO) were mixed and incubated at 37° C. for 15 minutes. To the reaction mixture, 1.0 ml of 0.2N NaOH and then 1.0 ml of n-butanol were added and voltex-mixed. Absorbance of n-butanol layer at 415 nm was measured by spectrophotometer. α-Glucosidase inhibitory activity was expressed as the IC$_{50}$ (μg/ml), the concentration at which the test compound inhibits 50% of the enzyme activity. IC$_{50}$ was determined from a standard curve of p-nitrophenol released when the assay was run without the test compound (0% inhibition) and when the assay was run without the enzyme (100% inhibition).

Results

Pradimicin Q showed the strongest α-D-glucosidase activity with an IC$_{50}$ value of 3 μg/ml. This value is significantly higher than that for benanomicin C which showed an IC$_{50}$ value of 62 μg/ml. In contrast, pradimicins A and L and N,N-dimethylpradimicin FA-2, all active as antifungal compounds, have no α-glucosidase inhibitory activity.

TABLE 6

| Compound | IC$_{50}$ (μg/ml) |
| --- | --- |
| Pradimicin A | >100 |
| N,N-dimethylpradimicin FA-2 | >100 |
| Pradimicin L | >100 |
| Benanomicin C | 62 |

TABLE 6-continued

| Compound | IC$_{50}$ (μg/ml) |
| --- | --- |
| Pradimicin Q | 3 |

It is apparent that the compound of the present invention exhibit high α-glucosidase inhibitory action. Pradimicin Q is, therefore, useful for inhibiting an increase in blood glucose in animals, including humans, and for treating animals, including humans suffering from conditions such as prediabetes, diabetes, obesity and adiposity.

Pradimicin Q is administered to the animal in need of such treatment in a therapeutically effective amount by any accepted routes, including intravenous, intramuscular, oral, intranasal, and for superficial infections, topical administration. Preferably, the compound of the invention is administered parenterally or orally. Preparations for parenteral administration include sterile aqueous or non-aqueous solutions, suspensions, or emulsions. They may also be manufactured in the form of sterile solid compositions which can be dissolved in sterile water, physiological saline, or some other sterile injectable medium immediately before use. Oral formulation may be in the form of tablets, gelatin capsules, powders, lozenges, syrups, and the like. For topical administration, the compound may be incorporated into lotions, ointments, gels, creams, salves, tinctures, and the like. Unit dosage forms may be prepared using methods generally known to those skilled in the art of pharmaceutical formulations.

It will be appreciated that, when treating a host according to the method of this invention, the actual preferred route of administration and dosage used will be at the sound professional discretion of the attending physician and will vary according to the severity of the condition to be treated, route of administration, and patient characteristics, such as age, body weight, rate of excretion, concurrent medications, and general physical condition.

EXAMPLE 1

Production of Pradimicin Q by Fermentation of *Actinomadura verrucosospora* subsp. *neohibisca*

A. Agar Slant

*Actinomadura verrucosospora* subsp. *neohibisca* strain R103-3 (ATCC No. 53930) was propagated on an agar slant of modified Bennett's medium at 28° C. for 14 days. The composition of the medium is soluble starch (Nichiden Kagaku) 0.5%, glucose 0.5%, fish meat extract (Mikuni Kagaku Sangyo) 0.1%, yeast extract (Oriental Yeast) 0.1%, NZ-case (Sheffield) 0.2%, NaCl 0.2%, CaCO$_3$ 0.1%, and agar 1.6%.

B. Seed Culture

A small portion of the microbial growth from the slant culture was inoculated to a 500-ml Erlenmeyer flask containing 100 ml of the vegetative medium consisting of soluble starch (Nichiden Kagaku) 1%, glycerol 1%, yeast extract (Oriental Yeast) 1%, peptone (Daigo Eiyo) 0.5%, NaCl 0.3%, and CaCO$_3$ 0.2%. The pH of the medium was adjusted to 7.0 before autoclaving. The seed culture was incubated at 28° C. for 7 days on a rotary shaker at 200 rpm.

C. Flask Fermentation

A 5 ml portion of the seed culture was transferred to a 500-ml Erlenmeyer flask containing 100 ml of the production medium (FR-17) consisting of soluble starch (Nichiden Kagaku) 1%, glucose 1%, sodium L-glutamate 0.1%, L-methionine 0.05%, L-arginine 0.05%, $(NH_4)_2SO_4$ 0.1%, $MgSO_4.7H_2O$ 0.05%, NaCl 0.05%, $CaCO_3$ 0.3%, $K_2HPO_4$ 0.6%, and salt solution 1% (v/v) ($FeSO_4.7H_2O$ 0.1 g, $ZnSO_4.7H_2O$ 0.1 g, and $MnCl_2.4H_2O$ 0.1 g in 1 liter of water). The pH of the medium was adjusted to 7.0 before autoclaving. The fermentation was carried out at 28° C. for 14 days on a rotary shaker (200 rpm). Antibiotic production in the fermentation broth was determined spectrophotometrically. The production of total pradimicin reached a maximum at 290 μg/ml on day 11.

EXAMPLE 2

Isolation of Pradimicin Q - Method 1

The fermentation broth pooled from fifty 500-ml Erlenmeyer flasks containing 100 ml broth in each flask was centrifuged at 5,000 rpm for 10 minutes at room temperature. The supernatant (4.5 L) was adjusted to pH 2.0 with 6N HCl and mixed with ethyl acetate (2 L). Ethyl acetate layer was washed twice with $H_2O$ (200 ml each) and concentrated to dryness to give a crude solid (453 mg). The crude solid was dissolved in $CH_3CN$-0.15% $KH_2PO_4$, pH 3.5 (1:1), and applied on a column of ODS-A60 (200 ml, Yamamura Chemical Lab.) which had been equilibrated with the same solvent mixture. Elution was carried out with the same solvent mixture. Fractions containing the pradimicin Q monitored by HPLC were pooled and concentrated to give a purple-red solid (190 mg). This solid (50 mg) was dissolved in 2 ml of MeOH-$H_2O$ (3:2) and subjected to a column of Sephadex LH-20 eluting with the same solvent mixture. A yellow-red powder (27 mg) was obtained as a free form. Purity of the compounds was determined by HPLC and was over 98%. The physico-chemical properties of pradimicin Q are given in Table 7.

TABLE 7

| Physico-Chemical Properties of Pradimicin Q | |
|---|---|
| Nature: | Purple-Red Powder |
| M.P. (dec.): | >200° C. |
| HR FAB(+)—MS m/z (M+H): | Found 465.0811 |
| | (Calcd: 465.0800) |
| Molecular Formula: | $C_{24}H_{16}O_{10}$ |
| UV λmax nm (ε) | |
| in MeOH: | 229(25,600), 288(19,500), 514(13,200) |
| in 0.01N HCl-50% MeOH: | 232(25,800), 289(20,600), 512(14,000) |
| in 0.01N NaOH-50% MeOH: | 242(20,000), 305(19,600), 549(15,900) |
| IR (KBr) cm$^{-1}$: | 3197, 1712, 1600, 1488, 1399, 1245, 1187 |
| $^1$H NMR(400MHz, DMSO-d$_6$) δ: | 2.50(s), 6.97(s), 4.55(dd, J=9.8 & 4.3), 2.66(dd, J=15,8 & 9.8), 3.10(dd, J=15.8 & 4.3), 6.63(d, J=2.4), 7.24(d, J=2.4) |
| $^{13}$C NMR(100 MHz DMSO-d$_6$)δ: | 187.5(s), 185.7(s), 171.5 (s), 165.5(s), 164.5(s), 156.0(s), 155.0(s), 153.9 (s), 146.1(s), 140.2(s), 137.0(s), 134.9(s), 131.6 (s), 119.2(s), 118.4(s), 118.3(d), 115.3(s), 110.6 (s), 109.1(s), 108.5(d), 108.2(d), 66.2(d), 30.7 |

TABLE 7-continued

| Physico-Chemical Properties of Pradimicin Q |
|---|
| (t), 21.6(q) |

EXAMPLE 3

Isolation of Pradimicin Q - Method 2

The fermentation broth (600 ml) was centrifuged at 5,000 rpm, and the supernate was applied on a column of HP-20 (200 ml). The resin was washed with water followed with acetone-$H_2O$ (3:2). Fractions containing compound Q were pooled and concentrated to dryness (1.4 g crude powder). The solid (170 mg) was dissolved in $CH_3CN$-$H_2O$ (1:4) and applied on a column of ODS-A60 (200 ml). The resin Was washed with $CH_3CN$-$H_2O$ (1:1). Fractions containing pradimicin Q were concentrated to dryness (27 mg powder). This solid (25 mg) was applied on a column of Sephadex LH-20 (70 ml) eluting with a mixture of MeOH-$H_2O$ (1:1, pH 8.5). A yellow-red powder (6.3 mg) was obtained as a sodium salt form. Compound Q showed weak antibacterial activity against *Bacillus subtilis* PCI-219 (125 μg/ml) and cytotoxic activity against mouse melanoma B16 cells with IC$_{50}$ at 75 μg/ml.

EXAMPLE 4

Production of Pradimicin Q by Fermentation of Strain A10102 (ATCC No. 55092)

Strain A10102 was grown in a 500-ml Erlenmeyer flask containing 100 ml of the vegetative medium consisting of soluble starch (Nichiden Kagaku) 1%, glycerol 1%, yeast extract (Oriental Yeast) 1%, peptone (Daigo Eiyo) 0.5%, NaCl 0.3%, and $CaCO_3$ 0.2%. The pH of the medium was adjusted to 7.0 before autoclaving. The seed culture was incubated at 28° C. for 7 days on a rotary shaker at 200 rpm.

A 5 ml portion of the seed culture was transferred to a 500-ml Erlenmeyer flask containing 100 ml of the production medium consisting of glucose 3%, Protein S (soybean flour, Ajinomoto) 3%, yeast extract 0.1%, $CaCO_3$ 0.3%, pH 7.0. The fermentation was carried out at 28° C. for 11 days on a rotary shaker at 200 rpm. Identification of pardimicin Q was done employing silica gel TLC (Merck) using a solvent system of MeOAc-n PrOH-28% $NH_4OH$ (45:105:60). Rf for pradimicin Q: 0.2–0.25 (cf pradimicin L: 0.35–0.4). From the TLC pattern, pradimicin Q was seen as the major product in the fermentation broth of strain A10102.

What is claimed is:

1. A compound having the formula

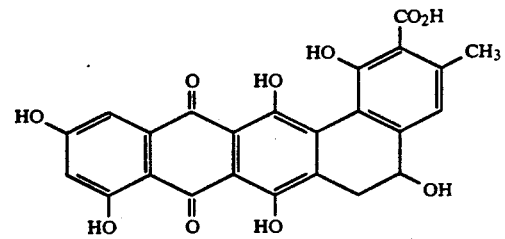

and its pharmaceutically acceptable base salts.

2. A pharmaceutically composition which comprises the compound of claim 1 and a pharmaceutically acceptable vehicle.

* * * * *